(12) United States Patent
Boese et al.

(10) Patent No.: US 8,023,707 B2
(45) Date of Patent: Sep. 20, 2011

(54) EVALUATION METHOD FOR MAPPING THE MYOCARDIUM OF A PATIENT

(75) Inventors: Jan Boese, Eckental (DE); Yu Deuerling-Zheng, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 762 days.

(21) Appl. No.: 12/079,142

(22) Filed: Mar. 25, 2008

(65) Prior Publication Data

US 2008/0240338 A1     Oct. 2, 2008

(30) Foreign Application Priority Data

Mar. 26, 2007   (DE) .................. 10 2007 014 883

(51) Int. Cl.
*G06K 9/00*     (2006.01)
*A61B 6/00*     (2006.01)
(52) U.S. Cl. .......................... 382/128; 378/4
(58) Field of Classification Search ................. 382/128, 382/129, 130, 131, 132, 133, 134; 378/4, 378/21–27, 62, 901; 600/407, 410, 425, 600/427; 128/920, 922; 424/9.4
See application file for complete search history.

(56) References Cited

U.S. PATENT DOCUMENTS

| | | | |
|---|---|---|---|
| 5,776,063 A * | 7/1998 | Dittrich et al. | 600/408 |
| 7,593,771 B2 * | 9/2009 | Yonce et al. | 607/4 |
| 7,805,181 B2 * | 9/2010 | Breeuwer | 600/419 |
| 7,930,014 B2 * | 4/2011 | Huennekens et al. | 600/407 |
| 2006/0120507 A1 | 6/2006 | Brunner et al. | |

FOREIGN PATENT DOCUMENTS

| | | |
|---|---|---|
| DE | 102004043809 A1 | 3/2006 |
| DE | 10 2004 057 308 A1 | 7/2006 |
| WO | 2006026976 A1 | 3/2006 |

OTHER PUBLICATIONS

Michael Bock, Stefan O. Schoenberg, Frank Floemer, and Lothar R. Schad; "Separation of Arteries and Veins in 3D MR Angiography Using Correlation Analysis"; Magnetic Resonance in Medicine; 2000; pp. 481-487; Wiley-Liss, Inc.
C. Michael Gibson, Albert Schö mig; "Coronary and Myocardial Angiography—Angiographic Assessment of both Epicardial and Myocardial Perfusion"; Review: Clinical Cardiology: New Frontiers; 2004; pp. 3096-3105; American Heart Association, Inc.
Arnoud W. J. Van 'T Hof, Aylee Liem, Harry Suryapranata, Jan C. A. Hoorntje; "Angiographic Assessment of Myocardial Reperfusion in Patients Treated with Primary Angioplasty for Acute Myocardial Infarction: Myocardial Blush Grade"; Circulation Journal of the American Heart Association; Sep. 20, 2006; pp. 2301-2306.

* cited by examiner

*Primary Examiner* — Abolfazl Tabatabai

(57) ABSTRACT

The invention relates to an evaluation method for mapping the myocardium of a patient, in particular the automated, functional evaluation, for instance the heart perfusion, in angiographic series with the steps: recording a series of angiographic recordings directly after administering a contrast agent to the patient; determining a reference area in an angiographic recording; determining a trend pattern of the contrast agent as a reference curve within the reference area from the series of angiographic recordings; obtaining trend patterns of the contrast agent from all areas of the angiographic recordings; determining the correlation between the trend patterns and the reference curve as a measure for the interrelationship between statistical variables, comparison with stored reference curve; comparison of the correlation coefficient with a threshold value; and reproduction of a marker identifying the myocardium.

16 Claims, 5 Drawing Sheets

EVALUATION METHOD FOR MAPPING THE MYOCARDIUM OF A PATIENT

CROSS REFERENCE TO RELATED APPLICATIONS

This application claims priority of German application No. 10 2007 014 883.8 filed Mar. 26, 2007, which is incorporated by reference herein in its entirety.

FIELD OF THE INVENTION

The present invention relates to an evaluation method for mapping the myocardium of a patient, in particular the automated functional evaluation, for instance the heart perfusion, in angiographic series. As the angiographic recording does not only detect the target structure, e.g. the myocardium, the identification of the target structure is the most important requirement for the functional evaluation. As a result of the high temporal resolution of the angiography, the method is based on analyses of gray scale value changes over time.

BACKGROUND OF THE INVENTION

The publications for angiographic heart perfusion analyses which have sporadically become known over the last few years essentially focus on the problem of "identifying the myocardium". This can either be obtained morphologically from an individual 2D angiographic frame or from the entire series by means of analyzing the temporal information. If the myocardium is found from a frame, it can be tracked along the time axis. If the myocardium is sought directly from the time information, the change in gray scale value enrichment and the movement must be separated from one another accordingly. Each method has advantages and disadvantages. None of the above is currently acknowledged as standard.

SUMMARY OF THE INVENTION

The invention addresses the object of preventing the disadvantages of the prior art cited in the introduction and specifying a method as well as an apparatus, which reliably determines the myocardium in a simple fashion.

This object is achieved by a method with the features of independent claim. Advantageous embodiments and developments are specified in the claims dependent thereon.

The object for the invention is achieved in accordance with the invention by the following steps:
a) Recording a series of angiographic recordings directly after administering a contrast agent to the patient,
b) Determining a reference area in an angiographic recording,
c) Determining a trend pattern of the contrast agent as a reference curve within the reference area from the series of angiographic recordings,
d) Obtaining trend patterns of the contrast agent from all areas of the angiographic recordings,
e) Determining the correlation between the trend patterns and the reference curve as a measure for the interrelationship between statistical variables, comparison with stored reference curve,
f) Comparison of the correlation coefficients with a threshold value and
g) Reproduction of a marker identifying the myocardium.

The aforementioned problem is solved using this correlation analysis of time-intensity curves of the local regions for instance. An angiographic series consists of a temporally consecutive recording of a scene, while the contrast agent flows into the vessel. As the inflow of the contrast agent into the vessel and myocardium has different trend patterns (along the time axis), the differential analysis of this trend pattern can reveal the tissue allocation.

The correlation is generally a measure for the interrelationship between two or more statistical variables. In our work, these variables are the sampled gray scale values of a pixel (or the mean gray scale value of a local region) over time. They are described below as a discrete time function.

Correlation is frequently used as a measure for the similarity of two functions. For this purpose, the so-called product moment correlation is usually calculated according to Bravais and Pearson. The resulting correlation coefficient reaches the value in the range [−1, 1]. A positive correlation has a similar interrelationship, i.e. X and Y increase or drop mutually. A negative correlation has an opposite interrelationship, i.e. X increases, when Y drops or vice versa. A correlation about zero signifies an interrelationship between the two curves.

$$c(X, Y) = \frac{1}{n}\sum_{i=1}^{n}\left(\frac{x_i - \bar{x}}{s_x}\right)\left(\frac{y_i - \bar{y}}{s_y}\right) \qquad (1)$$

$$= \frac{1}{n}\sum_{i=1}^{n}\left(\frac{x_i - \bar{x}}{\sqrt{\sum_{i=1}^{n}\frac{(x_i - \bar{x})^2}{n}}}\right)\left(\frac{y_i - \bar{y}}{\sqrt{\sum_{i=1}^{n}\frac{(y_i - \bar{y})^2}{n}}}\right)$$

$$= \frac{\sum_{i=1}^{n}(x_i - \bar{x})(y_i - \bar{y})}{\sqrt{\sum_{i=1}^{n}(x_i - \bar{x})^2 \sum_{i=1}^{n}(y_i - \bar{y})^2}}$$

with $$\bar{x} = \sum_{i=1}^{n} x_i \quad \bar{y} = \sum_{i=1}^{n} y_i$$

where
X, Y are vectors of two time-intensity curves,
$\bar{x}, \bar{y}$ are average values of X and Y,
c(X,Y) are the correlation coefficient of X and Y.

As the normalized correlation coefficient c(X,Y) provides a measure for the phase consistency of two functions, the amplitude and the actual functional values (gray scale values) are not taken into consideration. The amplitude and functional values of the time curves are however additional important features aside from the phases, which make a distinction between the myocardium and other structures in angiographic series.

The two features can be combined for instance as follows: A and B are two variables, the ratio between the smaller of A and B and the larger of A and B provides a measure for the distance between A and B. If A and B are identical, the measure reaches the maximum value of 1. If A and B are far apart from one another, the measure has the value of zero. This procedure is shown below using mathematical formulae:

$$Fa = \frac{\min(A_x, A_y)}{\max(A_x, A_y)} \in (0,1]$$

-continued $$Fg = \frac{\min(\overline{x}, \overline{y})}{\max(\overline{x}, \overline{y})} \in (0,1]$$

$$c'(X, Y) = F_a^p \cdot F_g^q \cdot c(X, Y) \in [-1,1] \quad (2)$$

In practice, the identification of the myocardium can be carried out as follows on the basis of correlation analyses.

A reference for the myocardium is first determined, e.g. with user interaction.

The correlation between the time function of each pixel and the time function of the reference is then calculated. The pixels, which show an adequate correlation with the reference, are referred to as myocardium. As the time curve of an individual pixel is often prone to noise, the correlation is preferably not calculated for each pixel, but instead for a local region, for instance a block of 4×4 pixels.

The correlation analysis can similarly be applied to the classification of the blood circulation of the myocardium. Two known classifications exist for the assessment of the perfusion following an acute myocardial infarction:

1. TIMI Myocardial Perfusion Grade (TMPG), as is described for instance in "Coronary and myocardial angiography: angiographic assessment of both epicardial and myocardial perfusion", by C. Gibson et al. [2], and
2. Myocardial Blush Grade (MBG) from "Angiographic Assessment of Myocardial Reperfusion in Patients Treated With Primary Angioplasty for Acute Myocardial Infarction: Myocardial Blush Grade" by Arnoud W. J. van 't Hof et al. [3].

During angiographic-based heart perfusion imaging, long recordings are carried out, with the recordings lasting until the contrast agent has flowed through the coronary vessels and can be visible in the myocardial muscle itself. This latter phase is referred to as "myocardial blush". The assessment of the "myocardial blush" is used to make statements about the vessel supply of the heart and to evaluate the success of therapies and/or a risk profile for the patient for instance.

MBG evaluates the perfusion according to the strength of the contrast increase. TMPG evaluates the perfusion according to the dynamics/time response of the contrast increase. The correlation analysis is thus more interesting for the evaluation using TMPG.

The gray scale value changes can be used advantageously to determine the correlation.

In accordance with the invention, the variables may be the scanned gray scale values of a pixel or the mean gray scale values of a local region over time, whereby the local area can be a block of 4×4 pixels.

The reference area can be determined manually or automatically, with the reference area being determined by means of differential analysis of the trend pattern in order to determine the tissue allocation in the case of automatic determination.

During the determination of the trend pattern of the contrast agent, advantageously only the angiographic recordings can be selected, said recordings corresponding to a specific heart phase.

The object is herewith achieved in accordance with the invention for an x-ray diagnostics device such that the image system has a serial image memory for an angiogram scene,
a computing unit for producing intensity-time curves from the angiogram scene,
a reference memory for storing an intensity-time curve of a selectable reference area,
a correlation stage for correlating the intensity-time curves from the computing unit with the intensity-time curve of the reference area stored in the reference memory,
a correlation image memory for storing the correlation image,
a threshold value stage for comparison with a threshold value determined in a threshold value memory and
a superimposition stage for superimposing the myocardium into an angiogram.

BRIEF DESCRIPTION OF THE DRAWINGS

The invention is described in further detail below with reference to exemplary embodiments illustrated in the figures, in which.

DETAILED DESCRIPTION OF THE INVENTION

Figure 1:
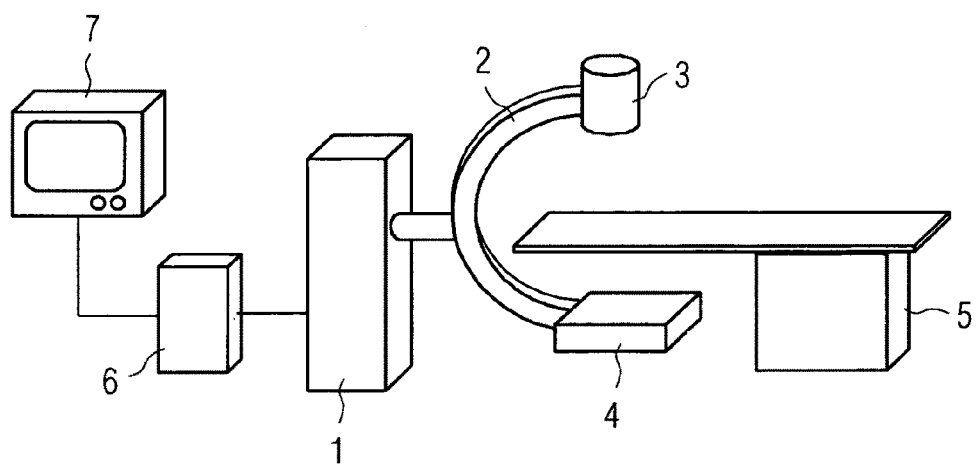
FIG. 1 shows an x-ray diagnostics device for implementing the method.

An x-ray diagnostics device for angiography is known from US 2006/0120507 A1, said device being shown in FIG. 1 by way of example and having a C-arm 2 which is mounted on a stand 1 in a rotatable fashion, on the ends of which an x-ray radiation source, for instance an x-ray emitter 3, and an x-ray detector 4 are attached.

The x-ray image detector 4 can be a rectangular, square or flat semiconductor detector, which is preferably made from amorphous silicon (aSi).

A patient positioning table 5 for recording a heart of a patient to be examined is located in the radiation path of the x-ray source 3 for instance. An image system 6 is connected to the x-ray diagnostic device, said image system 6 receiving and processing the image signals of the x-ray image detector 4. The x-ray images can then be viewed on a monitor 7.

Figure 2:
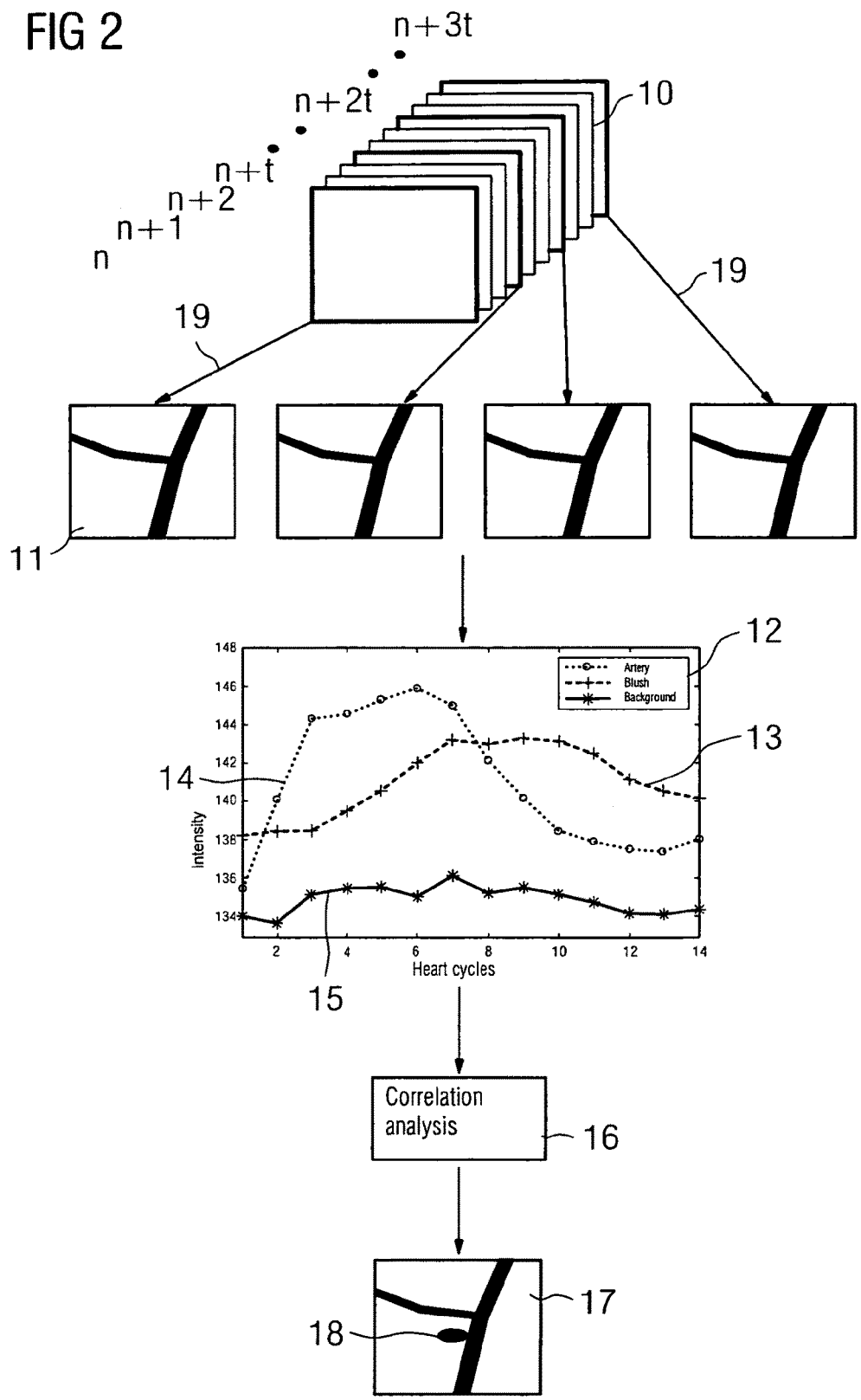
FIG. 2 shows a schematic illustration of the general procedure of the method according to the invention.

FIG. 2 shows a schematic representation of the general procedure. An angiogram series 10 is first produced by the x-ray diagnostics device according to FIG. 1. Intensity-time curves 12 or trend patterns are produced for each pixel or local area by the individual angiograms 11, said curves 12 or trend patterns being different depending on the type of tissue. In this diagram, the intensities are shown through the heart cycles. The intensity-time curve for blush 13 only has its maximum following the intensity-time curve for arteries 14, which is greater than that of the intensity-time curve for blush 13. The intensity-time curve for the background 15 has no defined maximum, but instead a statistical distribution.

A correlation analysis 16 is carried out by this intensity-time curve, in which analysis 16 the correlation between the individual pixels or local areas with an intensity-time curve of a reference area or pixel is determined, as is described again below.

To avoid movements of the patient during the production of the series of angiographic recordings the angiograms 11 are produced while the patient holds his/her breath in order to avoid breathing movements of the patient a retrospective ECG gating is used in order to avoid a movement of the heart during the evaluation, in which only the angiograms 11 are selected which correspond to a specific heart phase, as was indicated in FIG. 2.

The angiogram series 10 consists of a number of angiograms 11, which are numbered consecutively starting with the value n. In this way, the angiograms n, n+t, n+2t, n+3t etc. have been produced at the same point in time t of the heart cycle. To now prevent the heart movements from leading to an incorrect evaluation, not every angiogram 11 of the angiogram series 10 is used, as shown by the arrow 19, but instead only each angiogram 11 at the interval t.

Figure 3:
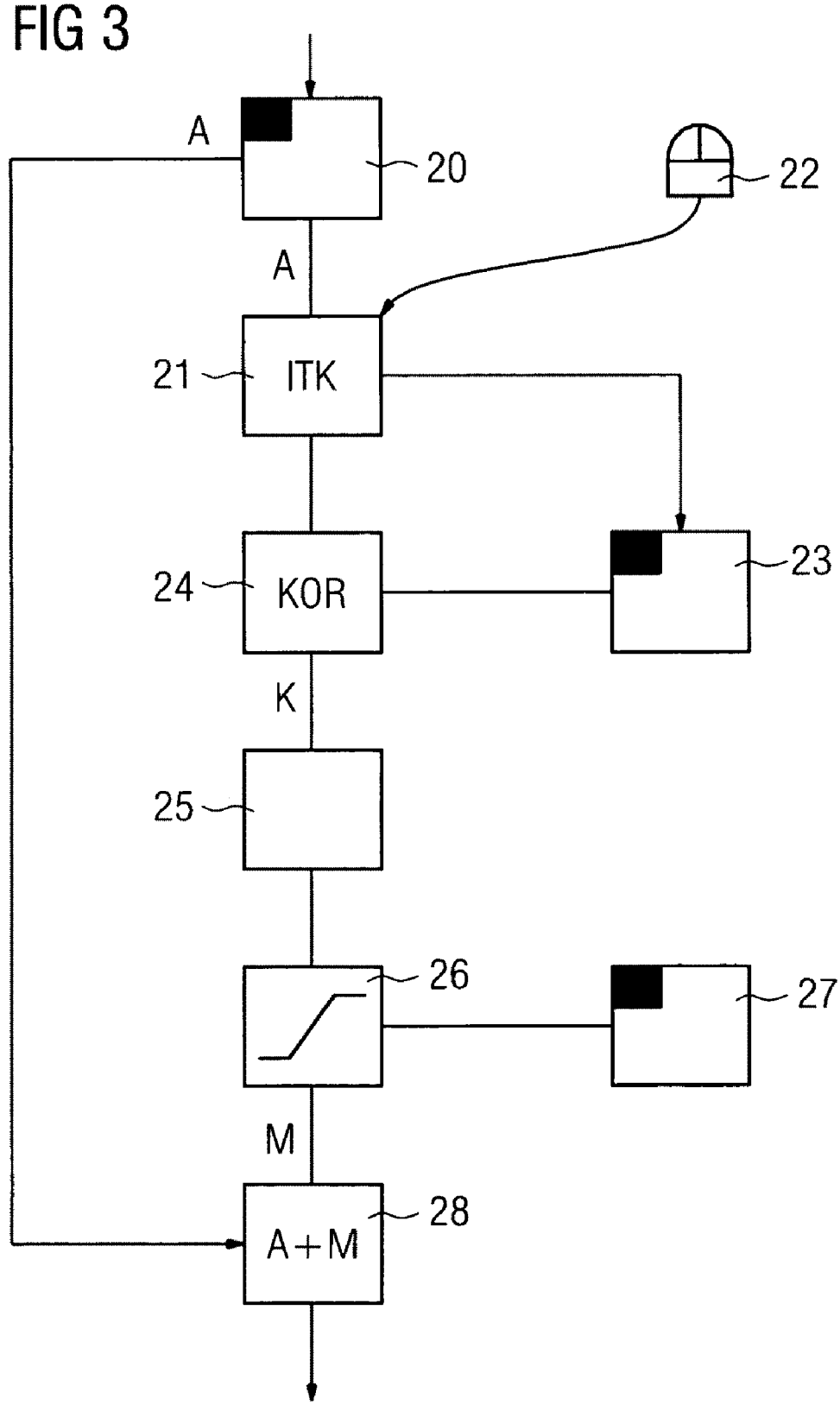
FIG. 3 shows a schematic design of the inventive correlation analysis in accordance with FIG. 2.

FIG. 3 now shows the set-up of the correlation analysis 16, which is part of the image system 6 of the x-ray diagnostic device according to FIG. 1. The angiogram series 10 is read into a serial image memory 20. Intensity-time curves ITK of individual pixels or local areas are produced from these angiograms A in a computing unit 21. Interaction by a user with a mouse 22 for instance marks a reference area in an angiogram, the intensity-time curve of which is stored in a reference memory 23.

In a subsequent correlation stage 24, the correlation of the individual intensity-time curves ITK of the individual pixels or local areas is determined from the computing unit 21 with the intensity-time curve of the reference area stored in the reference memory 23 according to the formula (1) or (2). The resulting correlation image K consisting of the correlation coefficients is stored in a correlation image memory 25 and is then compared in a threshold value stage 26 with a threshold value stored in a threshold value memory 27. A signal is then present at the output, which identifies the myocardium M. In a superimposition stage 28 this produces a colored or black superimposition of the myocardium M into the angiogram A.

Figure 4:
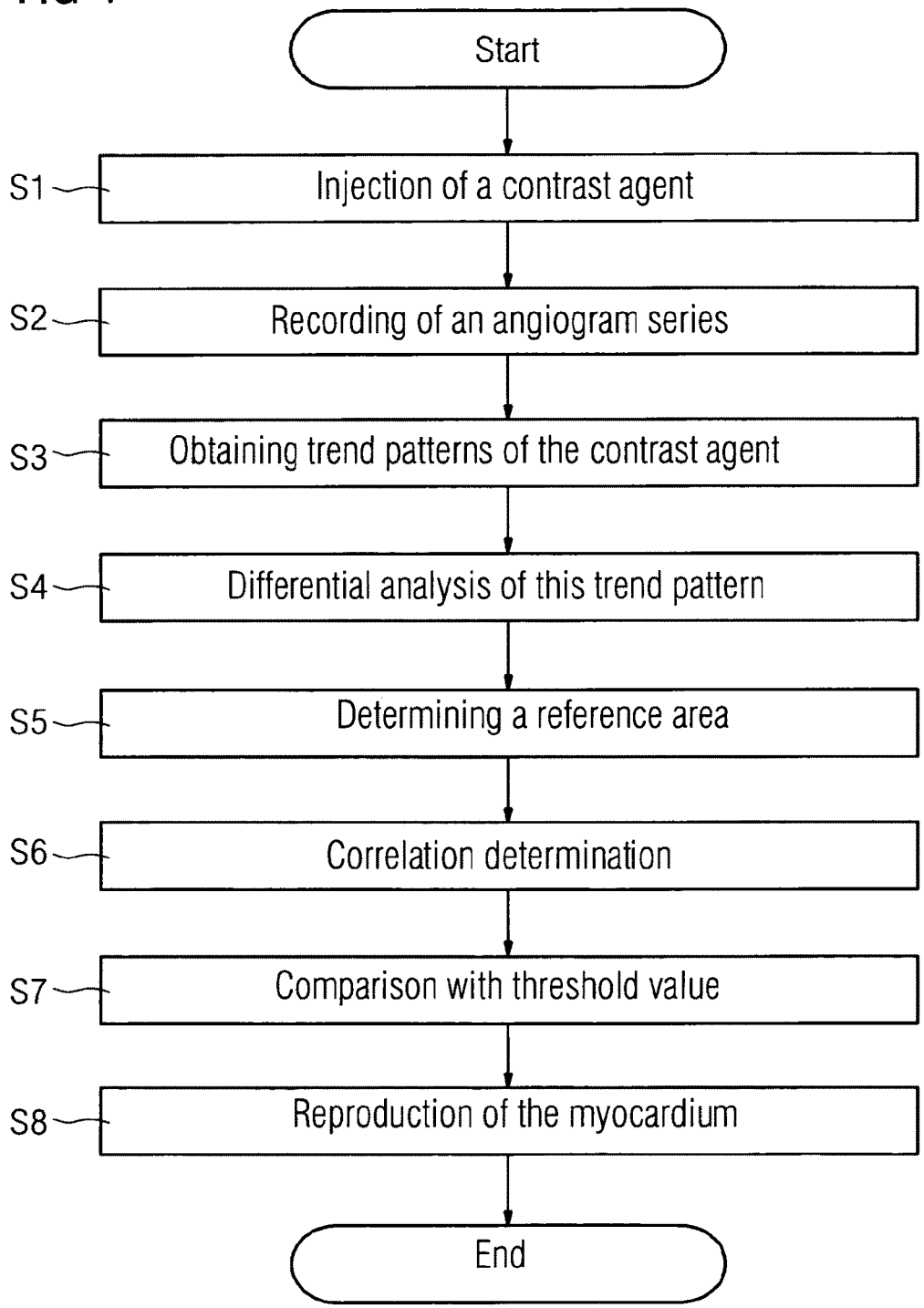
FIG. 4 shows the procedure.

The procedure according to the invention can be described briefly as follows and is shown in more detail in FIG. 4:

S1 Injection of a contrast agent into a coronary artery for instance;

S2 Recording of an angiographic series, consisting of a scene having temporally consecutive recordings, during which the contrast agent flows into the vessels;

S3 Obtaining trend patterns of the contrast agent as intensity-time curves of the individual pixels or local areas;

S4 Differential analysis of this trend pattern to determine the tissue allocation;

S5 Determination of a reference area with an associated intensity-time curve

S6 Determination of the correlation of the individual intensity-time curves of the individual pixels or local areas with the intensity-time curve of the reference area according to the formula (1) or (2).

S7 Comparison of the correlation coefficients with a threshold value, with the areas exceeding the threshold value identifying the myocardium;

S8 Reproduction of the myocardium, for instance as a superimposed marker in the angiogram.

Step S4 is used to automatically identify the myocardium. It can be omitted when the myocardium is identified manually, as described.

The actual procedure according to the method independent claim begins with step S2; however step S1 has to precede this step.

Figure 5:
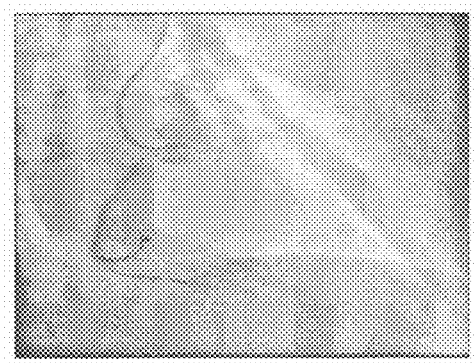
FIG. 5 shows an angiogram

FIG. 5 shows an angiographic image following the injection of a contrast agent into the right coronary artery (RCA). The myocardium is only marginally darker than the surrounding structure and can thus barely be seen.

Figure 6:
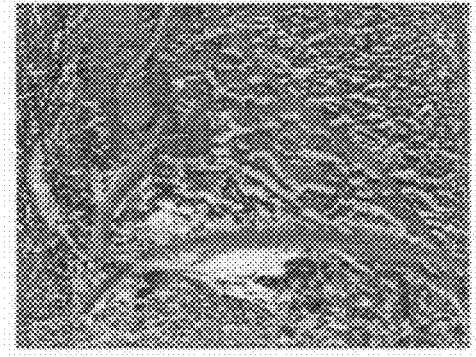
FIG. 6 shows a correlation image and
FIG. 7 shows an angiogram with a marked, detected myocardium.

In FIG. 6, the correlation image of the correlation coefficient shows the local correlation between the time-intensity curve of a reference region within the myocardium and the time-intensity curves of all local regions. Light indicates a high correlation here and dark a low correlation.

The reference curve of the myocardium is determined by means of user interaction, by selection using a mouse (not shown) for instance and by clicking on the area of the myocardium. The areas in which the correlation coefficient is greater than a specific threshold value are classified as myocardium.

The contrast increase by means of the contrast agent in the original angiogram according to FIG. 5 is barely visible, whereas the correlation image according to FIG. 6 quite clearly shows the myocardium as an interconnected pale area, and indicates a high correlation with the reference curve. The myocardium can be identified after a comparison of the correlation coefficients with the threshold value.

Figure 7:
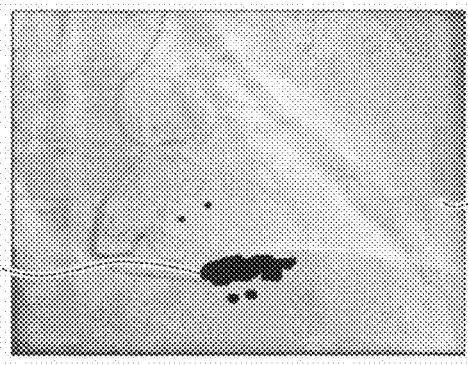

In FIG. 7, the regions identified as myocardium having a higher correlation coefficient than a threshold of 0.5 are marked with black.

Examination results from several angiography sequences of the right coronary artery show that the myocardium can be identified using this method according to the invention. However FIG. 7 shows some areas in which sporadically distributed areas in the background are incorrectly identified as the myocardium. These small areas do not interfere with the overall image with the large area of the myocardium.

Angiography with a high time resolution is above all referred to as the gold standard for coronary vessel imaging. The analysis of the time function in angiographic series is consequently very important. With the previous evaluation, the characteristic features of the time function, for instance the amplitude and the time of arrival of the maximum functional value, are extracted and analyzed. The disadvantages of this method are:

(1) the extraction of features is sensitive to noise and
(2) the data is not used completely in the analysis because only the features of the time functions are analyzed.

By contrast, correlation analyses are advantageous in that all data is used in the subsequent analysis, therefore it is thus also less sensitive to noise. Correlations can be calculated for functions relating to time or relating to the location. In the image processing, functions relating to the location are of particular interest. (The image is interpreted as a signal sequence relating to the location). In "Separation of Arteries and Veins in 3D MR Angiography Using Correlation Analysis" by Michael Bock et al. [1], correlations were used to separate the pulmonary arteries and veins from one another. The use of correlation analyses of the time function in angiographic series was previously little examined.

The inventive steps are described again in summary below:

(1) The first inventive step consists in using the correlation analysis of the time function in angiographic series. To this end, it is used for instance to identify the myocardium and to determine the perfusion in the myocardium. The correlation analysis can generally also be used for identifying other structures, e.g. segmentation of coronary arteries, provided the temporal course of the structures can be distinguished from one another.

(2) The second inventive step is the integration of additional features such as the amplitude and the value range of the gray scale values. In addition to the temporal course, these additional features provide important information relating to the gray scale values.

(3) However, the significance of the correlation analysis depends on how reliably the reference was determined. In principle, one pixel is sufficient if its time function represents the characteristic of the sought reference function. In practice, the time function of an individual pixel is often considerably affected by noises or movement. To prevent this, the reference function is calculated from a local region. This region can be selected by the user, by him/her designating a ROI using a mouse. The ROI can be square or a circle. With a square ROI, the user 2 has to select 2 corners, with a circular ROI, the user only has to select the central point; the radius of the circle can be determined either automatically or by the user.

The invention claimed is:

1. A method for mapping a myocardium of a patient, comprising:
   recording a series of angiographic recordings of the patient directly after administering a contrast agent to the patient by an imaging recording device;
   determining a series of trend patterns of the contrast agent in the angiographic recordings by a computing unit;
   selecting a reference area in one of the angiographic recordings by the computing unit;
   defining the trend pattern of the one of the angiographic recordings in the reference area as a reference curve by the computing unit;
   calculating a series of correlation coefficients between the trend patterns and the reference curve by the computing unit;
   comparing the correlation coefficients with a threshold value by the computing unit; and
   mapping the myocardium based on the comparison by the computing unit to determine a perfusion in the myocardium,
   wherein the correlation coefficients are determined as follows:

$$c(X, Y) = \frac{\sum_{i=1}^{n}(x_i - \bar{x})(y_i - \bar{y})}{\sqrt{\sum_{i=1}^{n}(x_i - \bar{x})^2 \sum_{i=1}^{n}(y_i - \bar{y})^2}}$$

with $$\bar{x} = \sum_{i=1}^{n} x_i \quad \bar{y} = \sum_{i=1}^{n} y_i$$

where
X, Y are vectors of two time-intensity curves,
$\bar{x}, \bar{y}$ are average values of X and Y,
c(X,Y) is the correlation coefficient of X and Y.

2. The method as claimed in claim 1, wherein the trend patterns are time-intensity curves.

3. The method as claimed in claim 1, wherein the correlation coefficients are calculated based on changes of gray scale value.

4. The method as claimed in claim 1, wherein the correlation coefficients are calculated based on a statistical variable.

5. The method as claimed in claim 4, wherein the statistical variable is a scanned gray scale value of a pixel over time.

6. The method as claimed in claim 4, wherein the statistical variable is a mean gray scale value of a local region over time.

7. The method as claimed in claim 6, wherein the local region is a block of 4 ×4 pixels.

8. The method as claimed in claim 1, wherein the reference area is determined manually.

9. The method as claimed in claim 1, wherein the reference area is determined automatically.

10. The method as claimed in claim 9, wherein the reference area is determined by differential analysis of the trend pattern of the one of the angiographic recordings.

11. The method as claimed in claim 1, wherein the correlation coefficients are determined as follows:

$$c'(X, Y) = F_a^p \cdot F_g^q \cdot c(X, Y) \in [-1,1]$$

with $$Fa = \frac{\min(A_x, A_y)}{\max(A_x, A_y)} \in (0,1]$$

and $$Fg = \frac{\min(\bar{x}, \bar{y})}{\max(\bar{x}, \bar{y})} \in (0,1].$$

12. The method as claimed in claim 1, wherein the angiographic recordings correspond to a specific heart phase.

13. The method as claimed in claim 1, wherein the myocardium is mapped as areas exceeding the threshold value.

14. An x-ray diagnostic device for mapping a myocardium of a patient, comprising:
   an imaging recording device that records a series of angiographic recordings of the patient directly after administering a contrast agent to the patient; and
   a computing unit that:
      determines a series of trend patterns of the contrast agent in the angiographic recordings,
      selects a reference area in one of the angiographic recordings,
      defines the trend pattern of the one of the angiographic recordings in the reference area as a reference curve,
      calculates a series of correlation coefficients between the trend patterns and the reference curve,
      compares the correlation coefficients with a threshold value, and
      mapping the myocardium based on the comparison,
   wherein the correlation coefficients are determined as follows:

$$c(X, Y) = \frac{\sum_{i=1}^{n}(x_i - \bar{x})(y_i - \bar{y})}{\sqrt{\sum_{i=1}^{n}(x_i - \bar{x})^2 \sum_{i=1}^{n}(y_i - \bar{y})^2}} \text{ with } \bar{x} = \sum_{i=1}^{n} x_i \_ \bar{y} = \sum_{i=1}^{n} y_i \text{ where}$$

X, Y are vectors of two time-intensity curves,
$\bar{x}, \bar{y}$ are average values of X and Y,
c(X,Y) is the correlation coefficient of X and Y.

15. The x-ray diagnostic device as claimed in claim 14, further comprising a memory that stores the angiographic recordings, the reference curve, or the threshold value.

16. The x-ray diagnostic device as claimed in claim 14, wherein the myocardium is an area that exceeds the threshold value.

* * * * *